United States Patent
Bornzin et al.

(10) Patent No.: US 8,781,605 B2
(45) Date of Patent: Jul. 15, 2014

(54) UNITARY DUAL-CHAMBER LEADLESS INTRA-CARDIAC MEDICAL DEVICE AND METHOD OF IMPLANTING SAME

(75) Inventors: Gene A. Bornzin, Simi Valley, CA (US); John W. Poore, South Pasadena, CA (US); Zoltan Somogyi, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/352,167

(22) Filed: Jan. 17, 2012

(65) Prior Publication Data

US 2013/0110219 A1    May 2, 2013

Related U.S. Application Data

(60) Provisional application No. 61/553,835, filed on Oct. 31, 2011.

(51) Int. Cl.
| | | |
|---|---|---|
| *A61N 1/372* | (2006.01) | |
| *A61N 1/362* | (2006.01) | |
| *A61B 17/34* | (2006.01) | |
| *A61N 1/375* | (2006.01) | |
| A61N 1/05 | (2006.01) | |
| A61N 1/39 | (2006.01) | |

(52) U.S. Cl.
CPC .......... *A61N 1/3756* (2013.01); *A61B 17/3468* (2013.01); *A61N 1/0573* (2013.01); *A61N 1/37205* (2013.01); *A61N 1/3962* (2013.01)
USPC ............................ 607/127; 607/126; 607/119

(58) Field of Classification Search
CPC ............ A61N 1/37205; A61N 1/3962; A61N 1/3756; A61N 1/0573; A61B 17/3468
USPC .................................................. 607/36, 127
See application file for complete search history.

(56) References Cited

U.S. PATENT DOCUMENTS

| | | |
|---|---|---|
| 3,835,864 A | 9/1974 | Rasor et al. |
| 3,835,869 A | 9/1974 | Newman et al. |

(Continued)

FOREIGN PATENT DOCUMENTS

| | | |
|---|---|---|
| EP | 1844812 A1 | 10/2007 |
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," PACE. 2007;30:748-754.

(Continued)

*Primary Examiner* — Carl H Layno
*Assistant Examiner* — Erin Piateski

(57) ABSTRACT

An assembly for introducing a leadless intra-cardiac medical device includes a sheath having an internal passage, wherein the sheath is configured to be maneuvered into the heart of the patient. A housing may be retained within the internal passage, wherein the housing is configured to be pushed out of the sheath, the housing having a first anchoring member configured to anchor the housing to a first implant location within the heart. The assembly may also include an electrode trailing the housing within the internal passage, wherein the electrode is also configured to be pushed out of the sheath. The electrode has a second anchoring member configured to anchor the electrode to a second implant location within the heart. A conductive wire connects the housing to the electrode, wherein movement of the housing out of the sheath causes the electrode to follow the movement to a distal end of the sheath.

11 Claims, 8 Drawing Sheets

(56) References Cited

U.S. PATENT DOCUMENTS

| | | | |
|---|---|---|---|
| 3,943,936 | A | 3/1976 | Rasor et al. |
| 4,987,897 | A | 1/1991 | Funke |
| 5,193,540 | A | 3/1993 | Schulman et al. |
| 5,358,514 | A | 10/1994 | Schulman et al. |
| 5,405,367 | A | 4/1995 | Schulman et al. |
| 5,411,535 | A | 5/1995 | Fujii et al. |
| 5,487,758 | A | 1/1996 | Hoegnelid et al. |
| 5,545,201 | A | 8/1996 | Helland et al. |
| 5,679,022 | A | 10/1997 | Cappa et al. |
| 5,814,089 | A | 9/1998 | Stokes et al. |
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,158,838 | B2 * | 1/2007 | Seifert et al. ............. 607/127 |
| 7,363,087 | B2 | 4/2008 | Nghiem et al. |
| 7,383,091 | B1 | 6/2008 | Chitre et al. |
| 7,513,257 | B2 | 4/2009 | Schulman et al. |
| 7,565,195 | B1 | 7/2009 | Kroll et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 | 12/2010 | Whitehurst et al. |
| 7,894,915 | B1 | 2/2011 | Chitre et al. |
| 7,899,555 | B2 | 3/2011 | Morgan et al. |
| 7,937,148 | B2 * | 5/2011 | Jacobson ..................... 607/9 |
| 7,945,333 | B2 * | 5/2011 | Jacobson ................... 607/59 |
| 8,010,209 | B2 | 8/2011 | Jacobson |
| 8,032,219 | B2 | 10/2011 | Neumann et al. |
| 2003/0163184 | A1 * | 8/2003 | Scheiner et al. ............ 607/122 |
| 2004/0015204 | A1 | 1/2004 | Whitehurst et al. |
| 2004/0015205 | A1 | 1/2004 | Whitehurst et al. |
| 2004/0147973 | A1 | 7/2004 | Hauser |
| 2005/0251202 | A1 * | 11/2005 | Ewers et al. ................ 606/213 |
| 2006/0009831 | A1 | 1/2006 | Lau et al. |
| 2006/0135999 | A1 | 6/2006 | Bodner et al. |
| 2007/0055310 | A1 | 3/2007 | Lau |
| 2007/0088396 | A1 | 4/2007 | Jacobson |
| 2007/0088400 | A1 | 4/2007 | Jacobson |
| 2007/0088418 | A1 * | 4/2007 | Jacobson ..................... 607/116 |
| 2008/0021336 | A1 * | 1/2008 | Dobak ......................... 600/508 |
| 2008/0097566 | A1 | 4/2008 | Colliou |
| 2008/0255647 | A1 | 10/2008 | Jensen et al. |
| 2009/0082827 | A1 * | 3/2009 | Kveen et al. ................. 607/36 |
| 2009/0082828 | A1 * | 3/2009 | Ostroff ......................... 607/36 |
| 2009/0281605 | A1 * | 11/2009 | Marnfeldt et al. .......... 607/116 |
| 2009/0299433 | A1 | 12/2009 | Dingman et al. |
| 2010/0010381 | A1 | 1/2010 | Skelton et al. |
| 2010/0069983 | A1 * | 3/2010 | Peacock et al. ................ 607/9 |
| 2010/0198288 | A1 * | 8/2010 | Ostroff ............................ 607/9 |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 * | 10/2011 | Griswold ..................... 607/126 |
| 2011/0251662 | A1 * | 10/2011 | Griswold et al. ............ 607/128 |

FOREIGN PATENT DOCUMENTS

| | | |
|---|---|---|
| WO | 2007047681 A2 | 4/2007 |
| WO | 2007047681 A3 | 9/2008 |
| WO | 2009039400 A1 | 3/2009 |
| WO | 2009078751 A1 | 6/2009 |
| WO | 2010088687 A1 | 8/2010 |

OTHER PUBLICATIONS

Brinker, Jeffrey A., "Endocardial Pacing Leads: The Good, the Bad, and the Ugly," PACE. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," PACE. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: A report of two cases," Heart. 2000;83:351-352.

Henz, Benhur D. MD et al., "Synchronous Ventricular Pacing without Crossing thetricuspid Valve or Entering the Coronary Sinus—Preliminary Results," J Cardiovasc Electrophysiol. 2009 (Dec.);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocarditis on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," PACE. 1990(Dec.-Pt II);13:1816-1822.

Stellbrink, Christoph et al.," Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. 2004(Nov.);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," PACE. 1999;22:823-824.

* cited by examiner

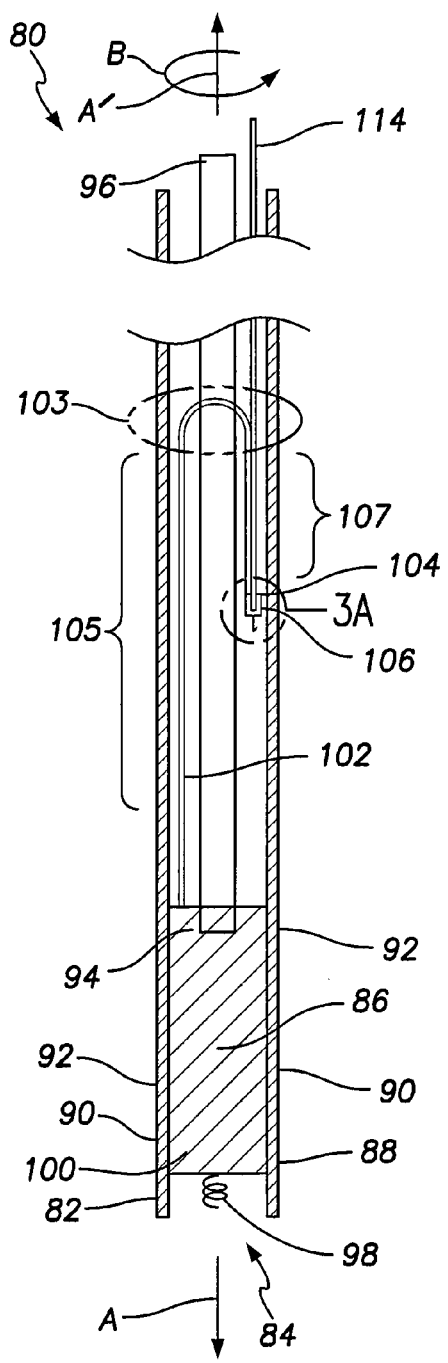
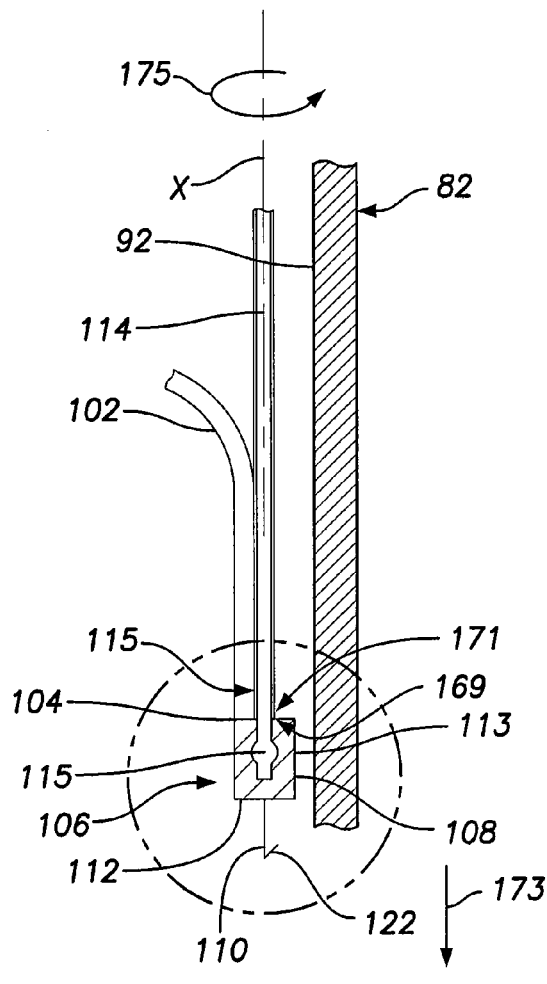
FIG. 2
FIG. 3A

UNITARY DUAL-CHAMBER LEADLESS INTRA-CARDIAC MEDICAL DEVICE AND METHOD OF IMPLANTING SAME

CROSS REFERENCE TO RELATED APPLICATIONS

This application relates to and claims priority benefits from U.S. Provisional Application No. 61/553,835, filed Oct. 31, 2011, entitled "Intra-Cardiac Implantation System and Method," which is hereby incorporated by reference in its entirety. This application also relates to U.S. patent application Ser. No. 13/352,005, filed Jan. 17, 2012, entitled "Multi-Piece Dual-Chamber Leadless Intra-Cardiac Medical Device and Method of Implanting Same", and Ser. No. 13/352,136, filed Jan. 17, 2012, entitled "Dual-Chamber Leadless Intra-Cardiac Medical Device with Intra-Cardiac Extension", which are hereby incorporated by reference in their entirety.

FIELD OF THE INVENTION

Embodiments of the present invention generally relate to implanted medical devices, and more particularly to unitary dual-chamber leadless intra-cardiac medical devices and methods of implanting such devices entirely within a heart of a patient. As used herein, the term "leadless" generally refers to an absence of electrically-conductive leads that traverse vessels outside of the intra-cardiac space, while "intra-cardiac" means generally, entirely within the heart and associated vessels, such as the SVC, IVC, CS, pulmonary arteries and the like. "Unitary" means generally formed as, or assembled into, a single structure, particularly in advance of implant into a body.

BACKGROUND OF THE INVENTION

Current implantable medical devices for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads are located within the heart, a substantial portion of the leads, as well as the IMD itself are outside of the patient's heart. Consequently, bacteria and the like may be introduced into the patient's heart through the leads, as well as the IMD, thereby increasing the risk of infection within the heart. Additionally, because the IMD is outside of the heart, the patient may be susceptible to Twiddler's syndrome, which is a condition caused by the shape and weight of the IMD itself. Twiddler's syndrome is typically characterized by a subconscious, inadvertent, or deliberate rotation of the IMD within the subcutaneous pocket formed in the patient. In one example, a lead may retract and begin to wrap around the IMD. Also, one of the leads may dislodge from the endocardium and cause the IMD to malfunction. Further, in another typical symptom of Twiddler's syndrome, the IMD may stimulate the diaphragm, vagus, or phrenic nerve, pectoral muscles, or brachial plexus. Overall, Twiddler's syndrome may result in sudden cardiac arrest due to conduction disturbances related to the IMD.

In addition to the foregoing complications, implanted leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM) are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, it would be highly desired for LLPM devices to have dual chamber pacing/sensing capability (DDD mode) along with other features, such as rate adaptive pacing.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communicate with one another to convey pacing and sensing information there between to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power.

Further, it is difficult to maintain a reliable wireless communications link between LLPM devices. The LLPM devices utilize low power transceivers that are located in a constantly changing environment within the associated heart chamber. The transmission characteristics of the environment surrounding the LLPM device change due in part to the continuous cyclical motion of the heart and change in blood volume. Hence, the potential exists that the communications link is broken or intermittent.

SUMMARY OF THE INVENTION

Certain embodiments provide an assembly for introducing a leadless intra-cardiac medical device within a heart of a patient. The assembly may include a sheath having an internal passage, wherein the sheath is configured to be maneuvered into the heart of the patient. A housing may be retained within the internal passage, wherein the housing is configured to be pushed out of the sheath, the housing having a first anchoring member configured to anchor the housing to a first implant location within the heart. The assembly may also include an electrode trailing the housing within the internal passage, wherein the electrode is also configured to be pushed out of the sheath. The electrode has a second anchoring member configured to anchor the electrode to a second implant location within the heart. A conductive wire connects the housing to the electrode, wherein movement of the housing out of the sheath causes the electrode to follow the movement to a distal end of the sheath.

The sheath may include a flexible, longitudinal, cylindrical open-ended tube defining the internal passage.

The assembly may also include a push rod within the sheath. The push rod may be removably connected to the housing. The push rod is configured to be engaged to push the housing out of the sheath. The push rod may also be configured to rotate the housing to screw the housing into the first implant location. The push rod may be threadably connected to the housing. Optionally, the push rod may be connected to the housing through an interference fit.

The first anchoring member may be an anchoring helix or barb. Similarly, the second anchoring member may be an anchoring helix or barb.

The assembly may also include a stylet removably connected to the electrode within the sheath. The stylet is configured to be engaged to push the electrode out of the sheath. The stylet may also be configured to rotate the electrode to screw the electrode into the second implant location.

The stylet may be threadably connected to the electrode. Optionally, the stylet may be connected to the electrode through an interference fit.

Certain embodiments provide a method of implanting a leadless intra-cardiac medical device. The method may include introducing an introducer assembly into one of an inferior vena cava or a superior vena cava of a heart, maneuvering the introducer assembly into a first chamber of the heart, pushing an housing out of a sheath of the introducer assembly toward a first implant location within the first chamber, anchoring the housing to the first implant location, moving the sheath away from the anchored housing, urging an electrode to a distal end of the sheath due to the pushing, anchoring, and moving, maneuvering the sheath to a second chamber of the heart, forcing the electrode into a second implant location within the second chamber, anchoring the electrode to the second implant location, moving the sheath away from the electrode after the anchoring; and removing the sheath from the heart.

The pushing a housing out of a sheath may include using a push rod within the sheath to push the housing out of the sheath. The anchoring the housing to the first implant location may include screwing the housing into the first implant location. The forcing the electrode into a second implant location may include using a stylet within the sheath to push the electrode into the second implant location. The method may also include detaching the stylet from the electrode. The detaching may include unscrewing the stylet from the electrode. The anchoring the electrode to the second implant location may include screwing the electrode into the second implant location.

BRIEF DESCRIPTION OF THE DRAWINGS

FIG. 2 illustrates a longitudinal axial view of a leadless intra-cardiac medical device (LIMD) within an introducer assembly.

FIG. 3A illustrates an electrode portion of the LIMD.

DETAILED DESCRIPTION

Figure 1:
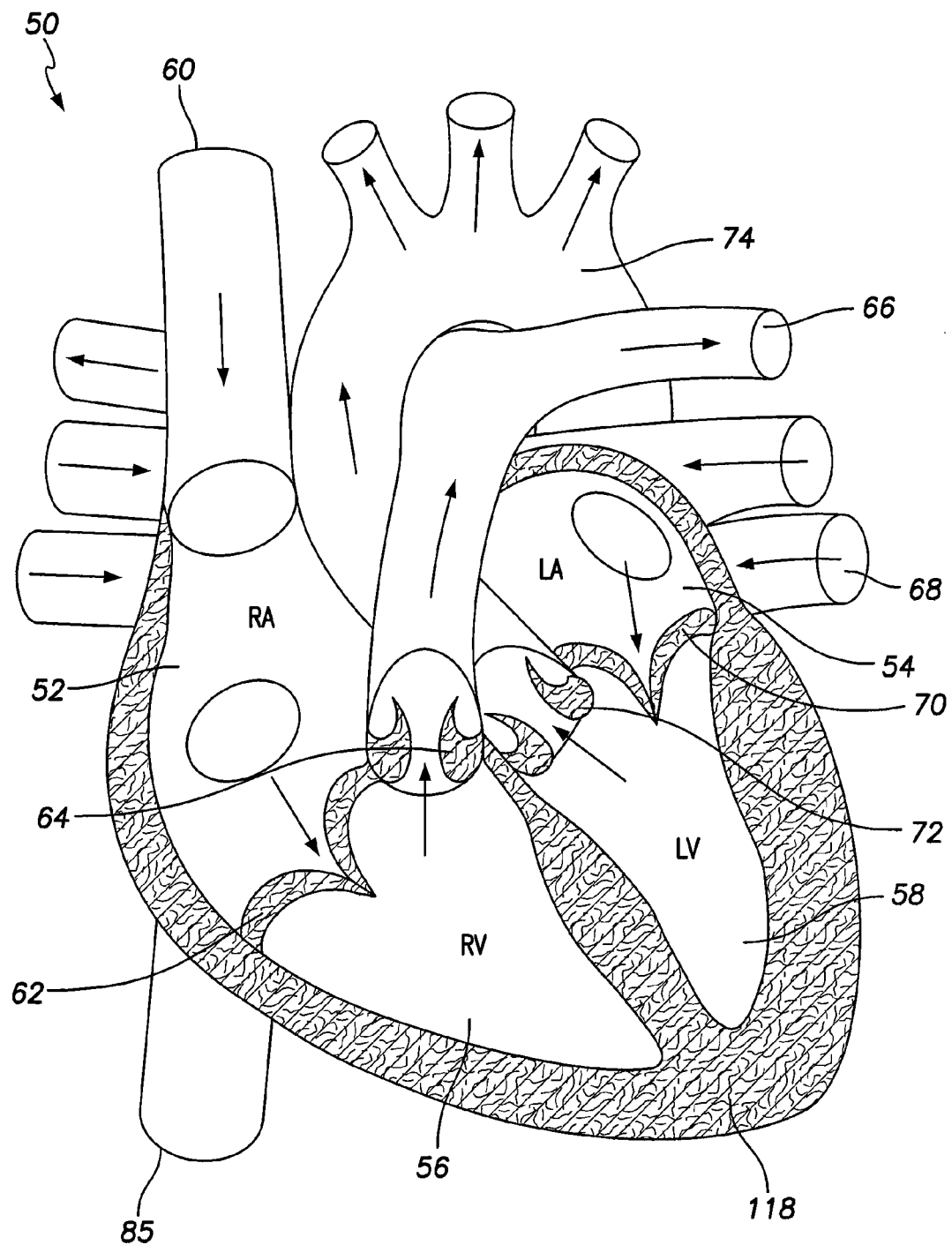
FIG. 1 illustrates a simplified view of a human heart.

FIG. 1 illustrates a simplified view of a human heart 50. The heart 50 is generally enclosed in a double-walled sac called a pericardium, which protects the heart 50. The outer wall of the heart includes three layers. The outer layer of the heart 50 is referred to as the epicardium, or visceral pericardium because it is also the inner layer of the pericardium. The middle layer of the heart 50 is referred to as the myocardium and is composed of muscle that contracts. The inner layer of the heart 50 is referred to as the endocardium and is in contact with blood that is pumped through the heart 50.

As shown in FIG. 1, the heart has four chambers, a right atrium 52, a left atrium 54, a right ventricle 56, and a left ventricle 58. In general, the atria 52, 54 are the receiving chambers, while the ventricles 56, 58 are the discharging chambers. Deoxygenated blood enters the heart 50 through the superior vena cava 60, for example, and passes into the right atrium 52. The blood is then pumped through the tricuspid valve 62 into the right ventricle 56 before being pumped out through the pulmonary valve 64 into the pulmonary artery 66. The blood is then oxygenated in the lungs and returns to the heart 50 through the pulmonary vein 68 into the left atrium 54, where it is then pumped through the mitral valve 70 and into the left ventricle 58. The oxygenated blood then travels from the left ventricle 58 through the aortic valve 72 and into the aorta 74, through which the oxygenated blood is then circulated throughout the body.

FIG. 2 illustrates a longitudinal axial view of a unitary leadless intra-cardiac medical device (LIMD) within an introducer assembly 80 with. The introducer assembly 80 includes a flexible, longitudinal, cylindrical open-ended sheath 82 defining a central internal passage 84. The sheath 82 may be a flexible tube formed of silicon rubber, for example, that is configured to be maneuvered through patient anatomy, such as veins and the heart. In this respect, the sheath 82 may be similar to that of a cardiac catheter.

A physician or surgeon operates the introducer assembly 80 at a proximal end (not shown). The proximal end may include controls that allow the sheath 82 to be bent, curved, canted, rotated, twisted, or the like, so as to be navigated through a patient's vasculature. In an embodiment, a distal end 88 of the sheath 82 may be bent, curved, canted, rotated, twisted, articulated, or the like through operation by the physician or surgeon manipulating the proximal end of the assembly 80.

The LIMD includes a housing 86, electrode 106 and conductive wire. The housing 86 is located at the distal end 88 of the sheath 82. The housing 86 contains electronics that allow the LIMD to function as one of various types of implantable devices, such as, for example, an implantable pacemaker, implantable cardioverter-defibrillator (ICD), neurostimulator, or the like. The LIMD may be configured for DDDR pacing (atrial and ventricular pacing, atrial and ventricular sensing, dual response and rate-adaptive, used for dual chamber pacemakers). As shown, outer walls 90 of the housing 86 slide along inner walls 92 of the sheath 82. The housing 86 is configured to be pushed out of, or ejected from, the sheath 82 in the direction of arrow A. In this respect, a proximal end 94 of the housing 86 connects to a push rod 96 that extends within the sheath 82. For example, the proximal end 94 may be connected to the push rod 96 through a threadable connection, an interference fit, or the like. The push rod 96 extends into a reciprocal cavity of the housing 86 and may be generally coaxial with the housing 86.

An anchoring member 98, such as a helical anchor extends from a distal end 100 of the housing 86. The helical anchor may be a coiled, helical wire having a sharp point at a distal end. While the anchoring member 98 is shown as a helical anchor, the anchoring member 98 may alternatively be a hook, barb, or the like, that is configured to secure the housing 86 into tissue of the heart wall. All or a portion of the anchoring member 98 may function as an electrode. Additional electrodes, such as ring electrodes, may be included on the housing 86

A conductive wire 102, which represents a housing-to-electrode wire segment, extends from the proximal end 94 of the housing 86 and is loaded within the sheath 82. The conductive wire 102 represents a non-lead wire segment that electrically couples components within the housing 86 to the electrode 106. The wire 102 has a "non-lead" structure in that remote manipulation of the wire 102 is not sufficient to locate the electrode 106 at a desired position. As shown in FIG. 2, the wire 102 includes a semi-loop 103 that curves from a straight segment 105 connected to the housing 86 and connects to another straight segment 107 that connects to an electrode 106. Thus, in the configuration shown in FIG. 2, there is slack in the wire 102. The wire 102 connects to a proximal end 104 of the electrode 106 that is also positioned within the sheath 82, but which trails the housing 86. The wire 102 includes one or more conductors within an insulated sheath. Multiple conductors may be braided together as a single electrical path or may be insulated from one another to provide a desired number of distinct electrical paths to/from the housing 86 and one or more electrodes 106. Optionally, a plurality of electrically separate wires 102 may be utilized when an equal plurality of electrodes 102 are provided.

FIG. 3A illustrates the electrode 106, according to an embodiment. The electrode 106 includes a main body 108 having an anchoring member 110, such as a barb extending from a distal end 112. Alternatively, the anchoring member 110 may be a helical anchor, or various other structures configured to anchor the electrode 106 into tissue of the heart wall. As noted above, the wire 102 that connects the electrode 106 to the housing 86 extends from the proximal end 104 of the electrode 106. All or a portion of the anchoring member 110 may function as an electrode. Additional electrodes, such as ring electrodes, may be included on the body 108.

The proximal end 104 of the electrode 106 also includes a tool receptacle 113. A stylet 114 includes a coupling member 115, for example, a threaded region, at a distal end 116 that connects to the tool receptacle 113 at the proximal end 104 of the electrode 106. As shown in FIG. 3A, the stylet 114 extends from the electrode 106 about a central axis X. As such, the stylet 114 is aligned generally coaxial with the electrode 106. The stylet 114 is configured to guide the electrode 106 to a desired portion of heart wall tissue. The distal end 116 of the stylet 114 fits into the electrode 106 through a threaded connection, a friction fit, a snap fit, or the like. The stylet 114 is configured to be removed from the electrode 106 once the electrode 106 is anchored into the atrial wall. That is, the strength of the connection between the distal end 116 of the stylet 114 and the tool receptacle 113 may be overcome by a pulling force on the stylet 114 once the electrode 106 is anchored into the atrial wall.

Referring to FIGS. 1-3A, in operation, the introducer assembly 80 is inserted into a vein of a patient and maneuvered toward the patient's heart. In particular, a physician maneuvers the introducer assembly 80 through human vasculature, such as veins, and into the heart 50, by way of the superior vena cava 60 or the interior vena cava 85 (shown in FIG. 1). During this time, a separate and distinct imaging system, such as a fluoroscopic imaging system, and/or a surgical navigation system may be used to assist in guiding the introducer assembly 80 into the heart 50. For example, a physician may view a real-time fluoroscopic image of the patient's anatomy to see the introducer assembly 80 being maneuvered through patient anatomy.

The introducer assembly 80 is maneuvered into the heart 50 through the interior vena cava 85 or the superior vena cava 60 and into the right atrium 52. The introducer assembly 80 is then passed through the tricuspid valve 62 and into the right ventricle 56. The introducer assembly 80 is then maneuvered toward the right ventricular apex 118 until the distal end 88 of the sheath 82 abuts against the apex 118. Once the distal end 88 of the sheath 82 contacts the ventricular wall defining the apex 118, the push rod 96 is pushed toward the apex 118 and the anchoring member 98 is pushed into tissue proximate the apex 118. During this time, the push rod 96 is also rotated in the direction of arc B (FIG. 2), thereby causing the housing 86 and the anchoring member 98 to rotate in a common direction. As such, the anchoring member 98 is screwed into the tissue of the heart wall and the housing 86 is anchored into the apex 118.

In embodiments described above, the housing 86 and/or electrode 106 are configured to rotate within the sheath. Optionally, the sheath 82 may include one or more anti-rotation keying features 169, 171 along at least one area on the inner wall 92. For example, a bump or other raised projection 171 may be formed to extend inward from the inner wall 92 and oriented to direct toward the electrode 106. The proximal end 104 of the electrode 106 is formed with a mating notch 169 therein. For example, when the projection 171 is provided on a post or other member projecting inward form the inner wall 92, the mating indent or notch 169 may be provided along the outside of the electrode 106. The projection 171 and notch 169 engage one another to prevent internal rotation of the electrode 106 within the sheath 82 while engaged. For example, the physician may desire that the electrode 106 not rotate relative to the sheath 82 while implanting the housing 86. The projection 171 and notch 169 cooperate to prevent rotation of the electrode 106. The anti-rotation keying feature 169, 171 may also be used to prevent rotations of the stylet 114 relative to the sheath 82. Optionally, the projection 171 and notch 169 may be reversed on the electrode 106 and sheath 82.

Once the housing 86 is implanted, it may become desirable for the electrode 106 to rotate within the sheath 82. Hence, the electrode 106 is dislodged from the projection 171 by advancing the electrode 106 in the longitudinal direction 173 along the sheath 82. Once the projection 171 and notch 169 are disengaged from one another, the electrode 106 may be freely rotated within the sheath 82 about axis 175, such as to screw an active fixation member into tissue of interest.

Optionally, instead of the anchoring member 98, a barb may extend from the distal end 100 of the housing 86. In this embodiment, the housing 86 may simply be pushed into the heart wall in order to anchor the housing 86 thereto, instead of also rotating the housing 86 in the direction of arc B.

Figure 4:
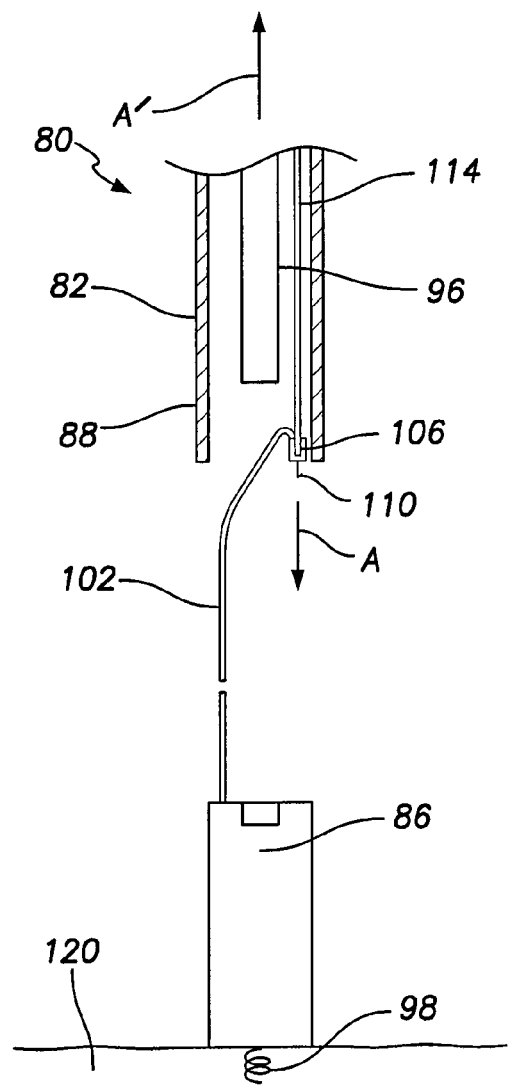
FIG. 4 illustrates an LIMD once ejected out of an introducer assembly.

Once the housing 86 is anchored to the heart wall, the push rod 96 is pulled back in the direction of arrow A' (FIG. 4). As the push rod 96 is pulled back, the anchoring force of the anchoring helix 98 (or barb) ensures that the housing 86 remains anchored to the heart wall. The anchoring force ensures that the push rod 96 separates from the housing 86 (as the push rod 96 may only be connected to the housing 86 through a relatively weak interference fit, for example).

After the push rod 96 separates from the housing 86, the sheath 82 is also pulled back in the direction of arrow A'. Because the housing 86 is now anchored to the heart wall, the sheath 82 also slides out of engagement with the housing 86. During this time, the conductive wire 102 is fed from the open distal end 88 as the sheath 82 continues to pull away from the housing 86. The conductive wire 102 tightens and exerts a pulling force on the electrode 106 in the direction of arrow A (FIG. 2), because the housing 86 is now anchored in a fixed position. As the sheath 82 continues to recede from the housing 86, the anchored housing 86 pulls on the electrode 106 through the tightening conductive wire 102 until the electrode 106 is proximate the distal end 88 of the sheath 82.

Figure 3B:
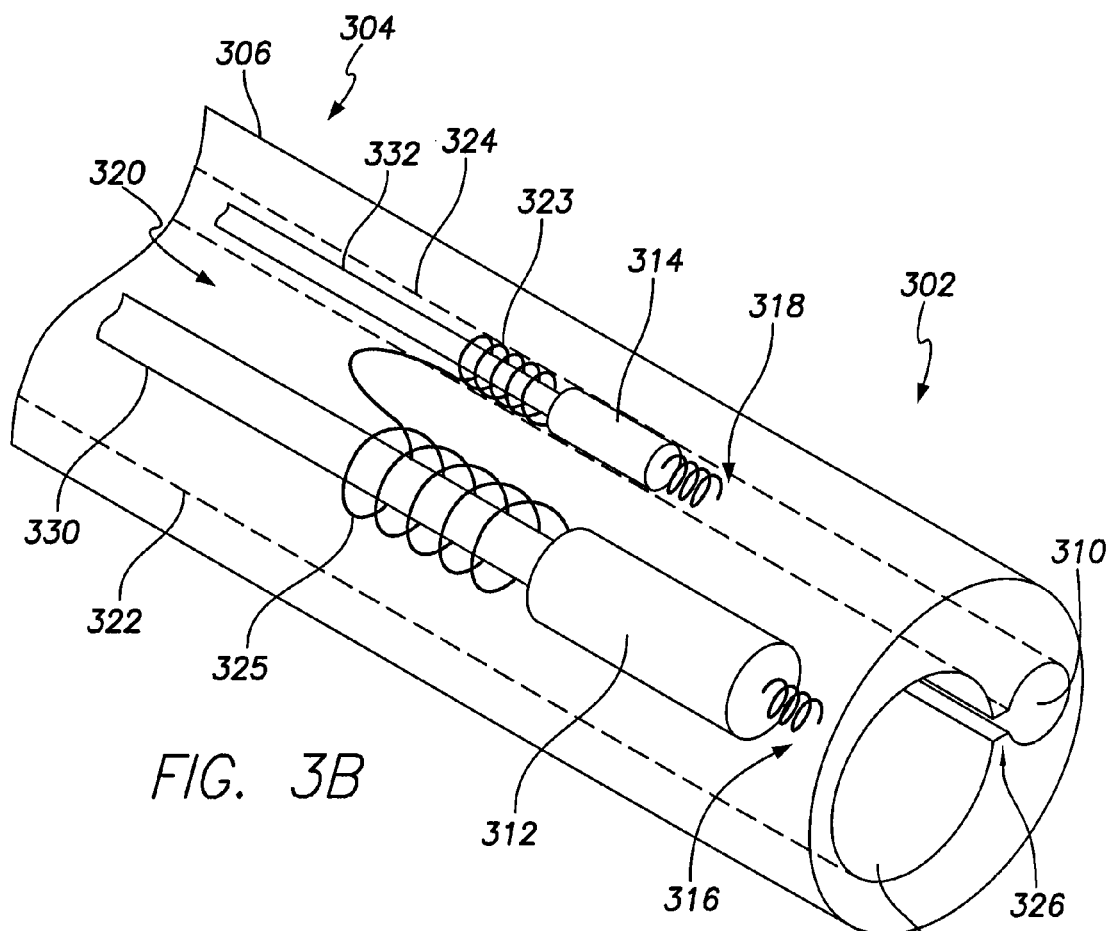
FIG. 3B illustrates a distal end of a sheath for an introducer.

FIG. 3B illustrates a distal end 302 of a sheath 304 for an introducer formed in accordance with an alternative embodiment. The sheath 304 generally has a circular outer perimeter wall 306. The sheath 304 includes at least two internal passages 308, 310 extending parallel to one another and along a length of the sheath 304. The passages 308, 310 open onto the distal end 302 and extend to the proximal end (not shown) where a physician operates user controls for the introducer. The passage 308 represents an IMD or primary passage, into which a housing 312 is loaded. The passage 310 represents an electrode or secondary passage, into which an electrode 314 is loaded. The housing 312 and electrode 314 may be loaded through proximal or distal ends into respective passages 308, 310 before or after the sheath 301 is navigated into the heart. The passages 308, 310 include corresponding inner walls 322, 324, respectively, that limit and guide movement of the housing 312 and electrode 314 along desired longitudinal paths. By way of example, the passages 308, 310 may have the same or different circular, oval, square or other cross-sections that permit or prevent a desired rotation by the housing 312 and electrode 314.

The housing 312 and electrode 314 both include active fixation members 316, 318, respectively, on an end thereof to be securely affixed to tissue of interest in a single or different chambers of the heart. A non-lead conductive wire 320 electrically interconnects the housing 312 and electrode 314. The wire 320 moves within the passages 308, 310 as the housing 312 and electrode 314 are shifted along the sheath 304 and implanted.

The passages 308, 310 are joined by a passage linking slot 326 that extends along at least a portion of the length of the passages 308, 310. The slot 326 opens on to the distal end 302 of the sheath 304. When the housing 312 and electrode 314 are loaded (either through the distal or proximal ends of the sheath 304) into the sheath 304, the wire 320 is loaded into the slot 324. When wire 320 travels along the slot 324 during implantation and is entirely discharged from the slot 324 at the distal end 302, once the housing 312 and electrode 314 are fully deployed and engaged to tissue of interest.

A pusher rod 330 and a stylet 332 are joined to corresponding ends of the housing 312 and electrode 314, respectively. The pusher rod 330 and stylet 332 control longitudinal and rotational movement of the housing 312 and electrode 314 during implanting. The pusher rod 330 has a proximal end that is manipulated by a physician to force the housing 312 out of the distal end 302 and to cause the housing 312 to rotate within the passage 308 and screw in the active fixation member 316. The stylet 332 has a proximal end that is manipulate by a physician to force the housing 312 out of the distal end 302 and to cause the housing 312 to rotate within the passage 308 and screw in the active fixation member 316. The stylet 332 has a proximal end that is manipulated by a physician to force the electrode 314 out of the distal end 302. The stylet 332 is also used by the physician to cause the electrode 314 to rotate within passage 310 and screw in the active fixation member 318. As the housing 312 and electrode 314 travel along passages 308, 310, the wire 320 moves between the passages 308, 310 and slides along the linking slot 326. The sheath 304 includes an outer envelope 334 that is smooth and continuous in cross-section, such as circular oval and the like.

Optionally, when the housing 312 and/or electrode 314 are loaded into the sheath 82, the wire 320 may be pre-wound by a desired number of turns 323, 325 around the pusher rod 330 and/or stylet 332, respectively. The wire 320 is pre-wound in a reverse direction opposite to the direction in which the active fixation member is turned. For example, as shown in FIG. 3B, when it is desirable to pre-wind the wire 320 about the stylet 332 and if the electrode 106 is expected to use 5-10 clockwise turns to screw in a helix, then the wire 320 may be pre-wound in an equal number of 5-10 turns 323 in the counterclockwise direction about the stylet 332.

Optionally, when desirable to pre-wind the wire 320 about the pusher rod 330, the wire 320 is wound a number of turns 325 in the clockwise or counterclockwise direction (opposite to the direction used to screw in a helix or other active fixation member).

Figure 3C:
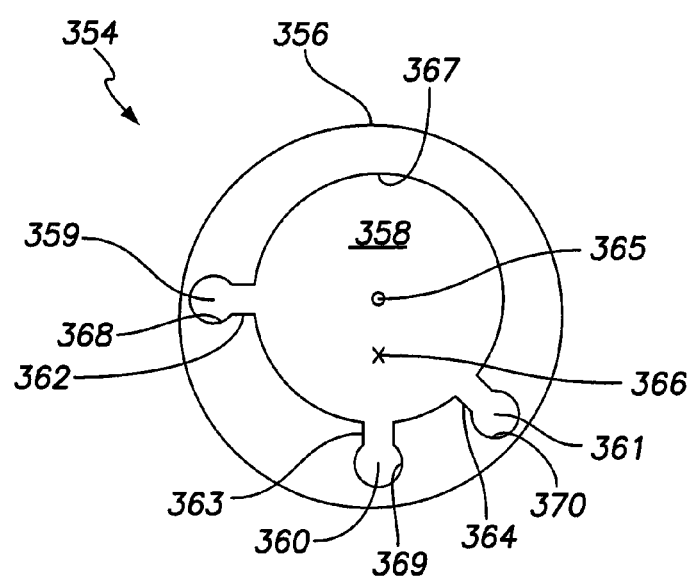
FIG. 3C illustrates a distal end plan view of a sheath.

FIG. 3C illustrates an end plan view of a sheath 354 formed in accordance with alternative embodiments. In FIG. 3C, the sheath 354 has an outer wall with an outer envelope 356 that has a continuous circular cross-section. The sheath 354 also includes multiple passages 358-361. For example, a primary passage 358 may be circular or oval with a larger cross sectional area than the cross-section of secondary passages 359-361. The passages 359-361 are connected to the passage 358 through linking slots 362-364, respectively. Optionally, the passages 359-361 may be connected to one another through linking slots (not shown). The passages 358-361 have various cross-sectional shapes, such as circular, oval, square, rectangular, triangular, hexagonal, polygonal and the like. The passages 359-361 are located along one arcuate circumferential portion of the passage 358. The passage 358 is located with the center 365 offset from a center 366 of the sheath 354. Centers of the passages 359-361 are radially displaced from the center 366 of the sheath 354. The passages 359-361 may have common or different diameters, cross-sectional shapes, spacings from the passage 358, and spacings between one another. Optionally, the passages 359-361 may be grouped closer to one another, or evenly distributed about the circumference of the passage 358. The passages 358-361 have smooth interior walls 367-370.

Figure 3D:
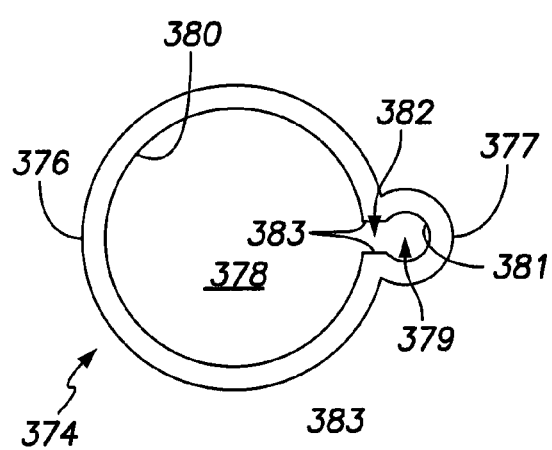
FIG. 3D illustrates a distal plan view of another sheath.

FIG. 3D illustrates a distal plan view of a sheath 374 formed in accordance with an embodiment. The sheath 374 has an outer envelope with an uneven contour to form a main outer wall 376 and an ancillary wall segment 377. The ancillary wall segment 377 is located along one side of the main outer wall 376.

A primary passage 378 is provided within the main outer wall 376, while at least one secondary passage 379 is provided within the ancillary wall segment 377. The passages 378, 379 have corresponding smooth inner walls 380, 381, respectively. The passages 378, 379 are joined and communicate with one another through a linking slot 382. The slot 382 has opposed facing sides 383 that extend along the length of the sheath 374. Optionally, more than one ancillary wall segment 377 and passage 379 may be provided about the passage 378.

FIG. 4 illustrates the housing 86 pushed out of the introducer assembly 80, according to an embodiment. As shown in FIG. 4, the housing 86 is anchored to the heart wall 120. As the sheath 82 is pulled back in the direction of arrow A', the housing 86 tugs on the electrode 106 in the direction of arrow A through the wire 102, and forces the electrode 106 to the distal end 88 of the sheath 82. The length of the wire 102 is sufficiently long that the electrode 106 is at the distal end 88 of the sheath 82 once the sheath 82 has been pulled back into the right atrium 52. Next, the electrode 106 is positioned next to an atrial wall, such as a right atrial appendage. The sheath 82 is then positioned to abut against the atrial wall tissue, such that the anchoring member 110 contacts the atrial wall tissue. The stylet 114 is then urged in the direction of arrow A into the atrial wall. The stylet 114 pushes the anchoring member 110 into the atrial wall 106. Referring to FIG. 3A, a reverse hook 122 of the anchoring member 110 ensures that the anchoring member 110, and therefore the electrode 106, is securely anchored into the atrial wall. The stylet 114 is then pulled away from the electrode 106 in the direction of arrow A' (FIG. 4). Because the electrode 106 is securely anchored into the atrial wall, the stylet 114 disconnects, or otherwise separates, from the electrode 106. Accordingly, an LIMD defined by the housing 86 connected to the electrode 106 through the conductive wire 102 is entirely contained within the heart 50.

Figure 5:
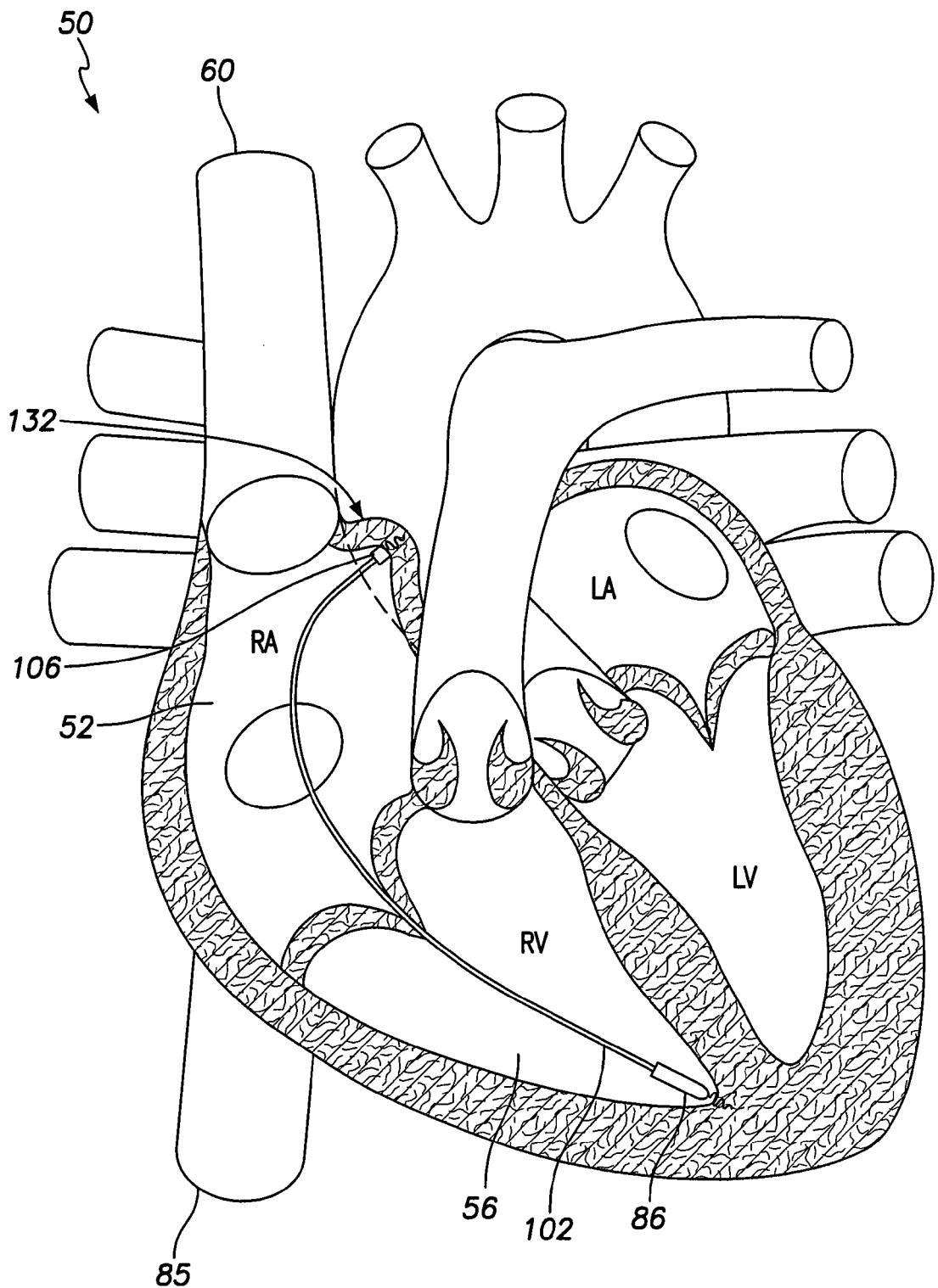
FIG. 5 illustrates a simplified view of LIMD within a patient's heart.

FIG. 5 illustrates a simplified view of LIMD 130 within a patient's heart. As noted above, the LIMD 130 includes the housing 86 anchored into the right ventricular apex 118 and the electrode 106 anchored into the right atrial appendage 132.

Figure 6:
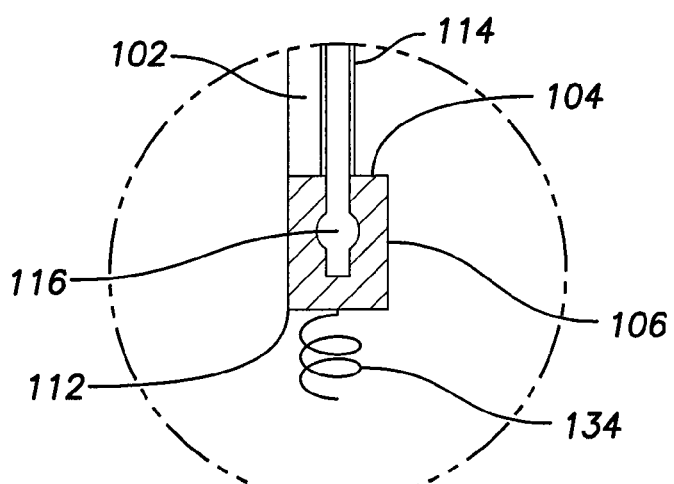
FIG. 6 illustrates another electrode portion of an LIMD.

FIG. 6 illustrates the electrode 106 according to an embodiment. In this embodiment, instead of a barb, an anchoring helix 134 may extend from the distal end 112 of the electrode 106. Thus, the stylet 114 may be used to push the electrode 106 into a heart wall, and then rotate to screw the electrode 106 in position. Notably, the electrode 106 and the housing 86 (shown in FIG. 2) may include either the barb or a helix as anchoring devices.

Figure 7:
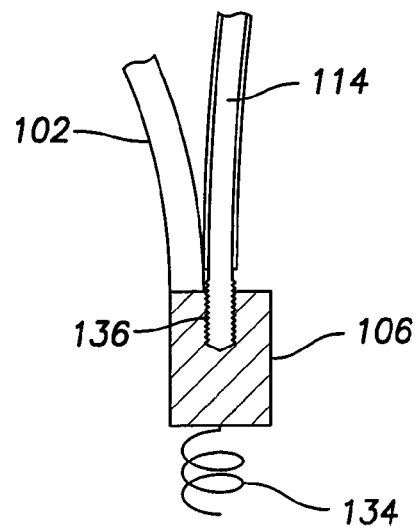
FIG. 7 illustrates another electrode portion of an LIMD.

FIG. 7 illustrates the electrode 106, according to an embodiment. In this embodiment, the stylet 114 is secured to the electrode 106 through a threadable interface 136. As such, instead of pulling the stylet 114 and the electrode apart, the stylet 114 may be unscrewed from the electrode 106. The threadable connection between the stylet 114 and the electrode 106 provides a more robust connection therebetween, as opposed to a relatively weak snap-fit or interference fit. Additionally, the push rod 96 (FIG. 2) may connect to the housing 86 through a similar threadable connection.

Referring to FIGS. 1-7, before the housing 86 and the electrode 106 are implanted within the heart 50, a pacing system analyzer (PSA) may be used to ensure adequate electrode placement, maintain basic cardiac functions, and evaluate pacing parameters for the housing 86 and the electrode 106. In general, the PSA may be used to test the housing 86 and the electrode 106 to ensure proper functionality.

The LIMD 130 is entirely within the heart 50. No portion of the LIMD 130 is outside the heart 50. The housing 86 and the electrode 106 may be programmed through a PSA. Alternatively, or additionally, the housing 86 and the electrode 106 may be programmed through a telemetry unit.

Figure 8:
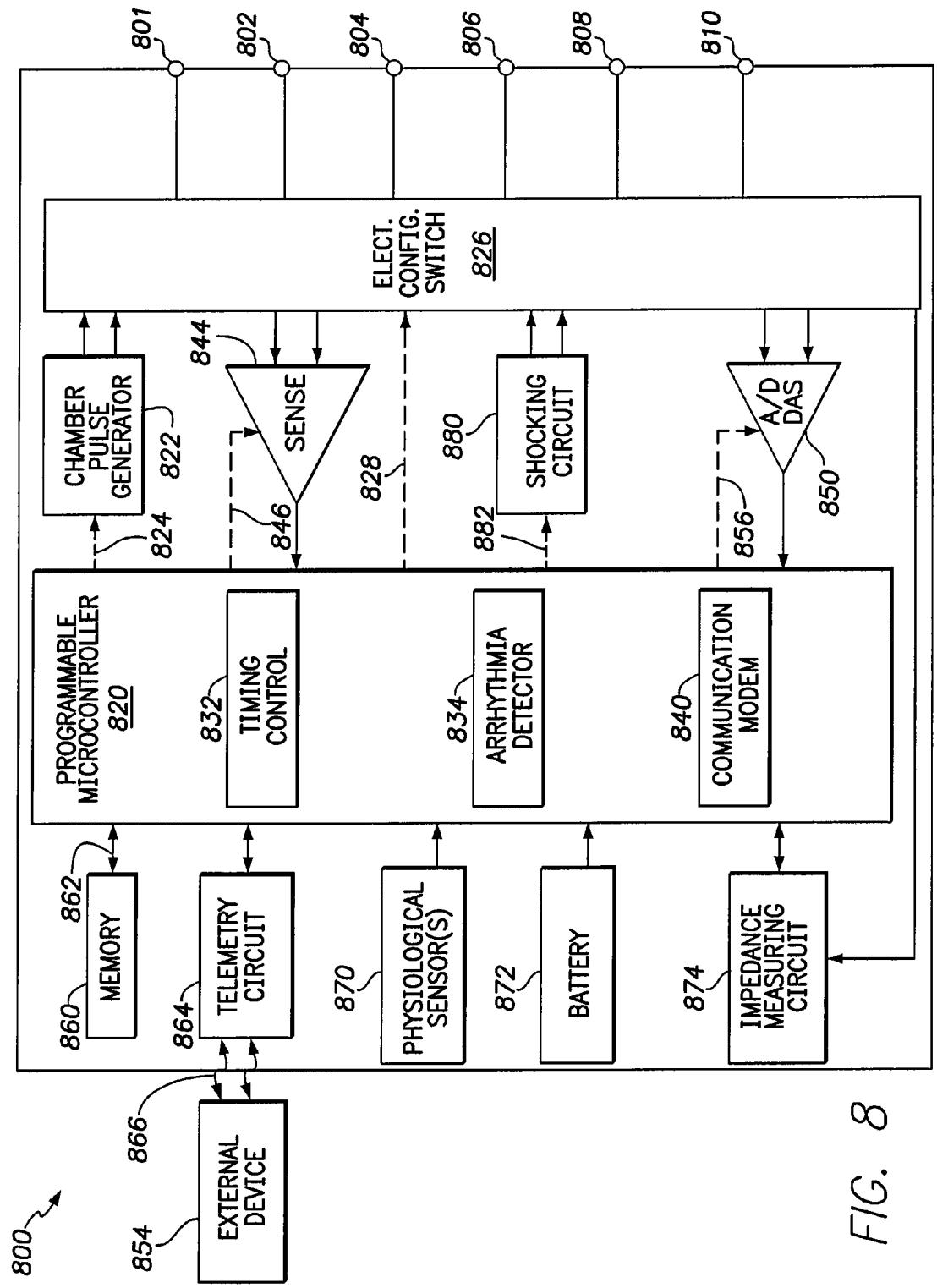
FIG. 8 illustrates an exemplary block diagram of the electrical components of an LIMD.

FIG. 8 shows an exemplary LIMD 800 configured for dual-chamber functionality from a primary location within a single side of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Electronics within the housing 801 further includes a plurality of terminals 802, 804, 806, 808, 810 that interface with electrodes of the LIMD. For example, the terminals may include: a terminal 802 that connects with a first electrode associated with the housing (e.g. a helix electrode) and located in a first chamber; a terminal 804 that connects with a second electrode associated with the housing (e.g., a ring electrode) and also located in the first chamber; a terminal 806 that connects with a third electrode associated with the electrode (e.g. a helix electrode) and located in a second chamber; a terminal 808 that connects with a fourth electrode associated with the electrode (e.g., a ring electrode); and an additional terminal, 810 that connect with one or more additional electrodes, if available. The type and location of each electrode may vary. For example, the electrodes may include various combinations of ring, tip, coil and shocking electrodes and the like.

The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 802 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the LIMD 800 may include multiple sensing circuit, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 808 within each respective tier of therapy.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The IMD 802 can further include magnet detection circuitry (not shown), coupled to the microcontroller 820, to detect when a magnet is placed over the unit. A magnet may be used by a clinician to perform various test functions of the unit 802 and/or to signal the microcontroller 820 that the external programmer 854 is in place to receive or transmit data to the microcontroller 820 through the telemetry circuits 864.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the can 800 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the unit 802, the physiologic sensor(s) 870 may be external to the unit 802, yet still be implanted within or carried by the patient. Examples of physiologic sensors might include sensors that, for example, sense respiration rate, pH of blood, ventricular gradient, activity, position/posture, temperature, minute ventilation (MV), and so forth.

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit 802 employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 811 to 40 joules), as controlled by the microcontroller 820. Such shocking pulses are applied to the patient's heart 808 through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

Figure 9:
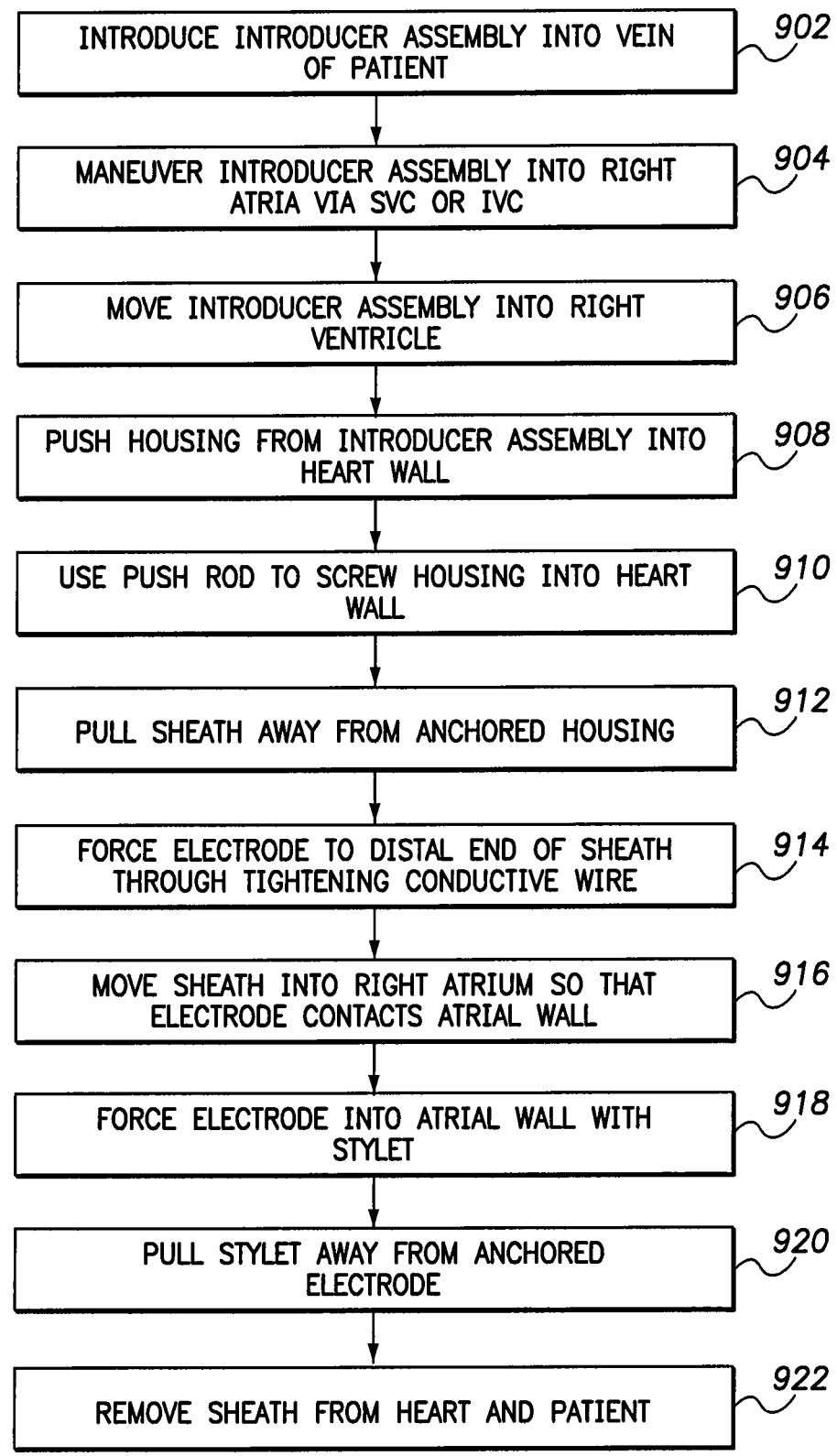
FIG. 9 illustrates a flow chart of a process of implanting an LIMD.

FIG. 9 illustrates a flow chart of a process of implanting an LIMD. At 902, the introducer assembly is introduced into a vein of a patient. Then, at 904, the introducer assembly is maneuvered into the right atrium of the patient through the superior vena cava or the inferior vena cava. Next, the introducer assembly is maneuvered into the right ventricle at 906.

When the introducer assembly is close to the desired location for implantation, the housing portion of the LIMD is pushed out of the sheath of the introducer assembly into the heart wall at 908. At 910, the push rod may be used to screw the housing into the heart wall. At 912, the sheath is then pulled away from the anchored housing. During this time, the push rod separates from the housing. Further, the electrode portion of the LIMD is forced to the distal end of the sheath through the conductive wire at 914.

Next, the sheath is moved into the right atrium so that the electrode contacts a desired implantation site on the atrial wall at 916. Then, at 918, the electrode is forced into the atrial wall with the stylet. At 920, the stylet is then pulled away from the anchored electrode, which separates the stylet from the electrode. Finally, at 922, the sheath is removed from the heart and the patient, leaving only the intra-cardiac system within the heart.

Thus, embodiments provide a method of implanting an LIMD configured to be entirely within a heart of a patient. Embodiments provide a system and method for dual chamber pacing, such as DDDR pacing, without leads that connect a device that is external to the heart. Unlike a conventional IMD, embodiments provide an LIMD that has no components outside the heart, thereby providing: a low infection rate, elimination of Twiddler's syndrome, greater patient comfort, little or no skin erosion, and elimination of other problems associated with conventional pacemaker implantation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An assembly for introducing a leadless intra-cardiac medical device within a heart of a patient, said assembly comprising:

a sheath having a first internal passage and a second internal passage, wherein the first internal passage and the second internal passage extend parallel to one another along a length of the sheath, wherein the sheath is configured to be maneuvered into the heart of the patient;

a first body having a housing retained within the first internal passage, wherein the housing is configured to be pushed out of the sheath, the housing having a first anchoring member configured to anchor the housing to a first implant location within the heart;

a second body having an electrode trailing the housing within the second internal passage, wherein the second body is discrete from the first body, wherein the electrode is also configured to be pushed out of the sheath, the electrode having a second anchoring member configured to anchor the electrode to a second implant location within the heart; and a conductive wire mechanically and electrically connecting the housing to the electrode, wherein movement of the housing out of the sheath causes the electrode to follow the movement to a distal end of the sheath due to the conductive wire.

2. The assembly of claim 1, wherein the sheath comprises a flexible, longitudinal, cylindrical open-ended tube defining the first internal passage and the second internal passage.

3. The assembly of claim 1, further comprising a push rod within the first internal passage and a stylet within the second internal passage, the push rod being removably connected to the housing and the stylet being removable connected to the electrode, wherein the push rod is configured to be engaged to push the housing out of the first internal passage and the stylet is configured to be engaged to push the electrode out of the second internal passage.

4. The assembly of claim 3, wherein the push rod is also configured to rotate the housing to screw the housing into the first implant location, and wherein the stylet is also configured to rotate the electrode to screw the electrode into the second implant location.

5. The assembly of claim 3, wherein the push rod is threadably connected to the housing, and wherein the stylet is threadably connected to the electrode.

6. The assembly of claim 3, wherein the push rod is connected to the housing through an interference fit, and wherein the stylet is connected to the electrode through an interference fit.

7. The assembly of claim 1, wherein the first anchoring member is an anchoring helix or barb.

8. The assembly of claim 1, wherein the second anchoring member is an anchoring helix or barb.

9. The assembly of claim 1, further comprising a passage linking slot joining the first internal passage to the second internal passage.

10. The assembly of claim 9, wherein the passage linking slot extends along a portion of the length of the first internal passage and the second internal passage.

11. The assembly of claim 9, wherein the conductive wire is loaded into the passage linking slot.

* * * * *